United States Patent
Lin

(10) Patent No.: US 9,603,527 B2
(45) Date of Patent: Mar. 28, 2017

(54) PERSON POSITIONING AND HEALTH CARE MONITORING SYSTEM

(71) Applicant: CHUNG HUA UNIVERSITY, Hsinchu (TW)

(72) Inventor: Jium Ming Lin, Hsinchu (TW)

(73) Assignee: Chung Hua University, Hsinchu (TW)

( * ) Notice: Subject to any disclaimer, the term of this patent is extended or adjusted under 35 U.S.C. 154(b) by 124 days.

(21) Appl. No.: 14/448,236

(22) Filed: Jul. 31, 2014

(65) Prior Publication Data

US 2016/0034731 A1 Feb. 4, 2016

(51) Int. Cl.
*G06K 7/10* (2006.01)
*A61B 5/00* (2006.01)
(Continued)

(52) U.S. Cl.
CPC .......... *A61B 5/0026* (2013.01); *A61B 5/002* (2013.01); *A61B 5/1113* (2013.01); *G01S 5/16* (2013.01); *A61B 5/021* (2013.01); *A61B 5/02438* (2013.01); *A61B 5/1117* (2013.01); *A61B 5/1121* (2013.01); *A61B 2503/08* (2013.01); *A61B 2562/0219* (2013.01)

(58) Field of Classification Search
CPC .............. G06K 7/10366; A61B 5/0026; A61B 2019/448
See application file for complete search history.

(56) References Cited

U.S. PATENT DOCUMENTS 5,917,425 A 6/1999 Crimmins et al.
2005/0242947 A1* 11/2005 Burneske ............ G01C 21/005
340/539.13
(Continued)

FOREIGN PATENT DOCUMENTS

CN 101425149 10/2010
TW M243179 9/2004
(Continued)

OTHER PUBLICATIONS

Office Action and Search Report dated Sep. 21, 2015 from the Taiwan counterpart application 103126141.
(Continued)

*Primary Examiner* — Nabil Syed
(74) *Attorney, Agent, or Firm* — WPAT, P.C., Intellectual Property Attorneys; Anthony King

(57) ABSTRACT

A person positioning and health care monitoring system includes a monitoring center, a RFID tag device, and a tracking module. The monitoring center includes positioning data corresponding to a target. The RFID tag device is located on the target and includes a memory storing a target identification (ID) number and an infrared LED. Each tracking module includes infrared cameras and an RFID device. The tracking module uses the RFID device to communicate with the RFID tag device so as to receive the target identification (ID) number. The tracking module communicates with the monitoring center so as to provide the target identification (ID) number and orientation data corresponding to the target for the monitoring center. The monitoring center determines coordinates of the target according to coordinates of the tracking module and the orientation data corresponding to the target.

15 Claims, 8 Drawing Sheets

(51) Int. Cl.
*A61B 5/11* (2006.01)
*G01S 5/16* (2006.01)
*A61B 5/021* (2006.01)
*A61B 5/024* (2006.01)

(56) References Cited

U.S. PATENT DOCUMENTS

| | | | |
|---|---|---|---|
| 2006/0209303 A1* | 9/2006 | Ohta | G01S 17/89 356/400 |
| 2007/0273522 A1* | 11/2007 | Dembo | G01S 13/878 340/572.1 |
| 2011/0109434 A1* | 5/2011 | Hadsall, Sr. | G08B 21/22 340/8.1 |
| 2011/0169613 A1* | 7/2011 | Chen | G01S 13/4445 340/10.4 |
| 2011/0199216 A1* | 8/2011 | Flinsenberg | A61B 5/1117 340/573.1 |
| 2011/0205077 A1* | 8/2011 | Cavallaro | A63B 24/0021 340/686.6 |
| 2012/0126973 A1* | 5/2012 | DeAngelis | A63B 24/0021 340/539.13 |
| 2012/0223813 A1* | 9/2012 | Baxter | E21B 44/00 340/10.1 |
| 2012/0233105 A1* | 9/2012 | Cavallaro | G01S 5/16 706/46 |
| 2013/0169415 A1* | 7/2013 | Bellows | G06K 7/0008 340/10.1 |
| 2015/0070319 A1* | 3/2015 | Pryor | G06F 3/0425 345/175 |

FOREIGN PATENT DOCUMENTS

| | | |
|---|---|---|
| TW | 201123038 | 7/2011 |
| TW | I388205 | 3/2013 |

OTHER PUBLICATIONS

English abstract translation of the Office Action dated Sep. 21, 2015 from the Taiwan counterpart application 103126141, TW 201123038, TW M243179, TW I388205 and CN 101425149.

* cited by examiner

PERSON POSITIONING AND HEALTH CARE MONITORING SYSTEM

BACKGROUND

1. Technical Field

The present invention relates to a person positioning and health care monitoring system.

2. Related Art

Due to extended lifespans of human beings, there are ever increasing numbers of older people in the world. In order to take care of older individuals, nursing homes are provided for their assistance.

However, although nursing homes have professional care-givers to assist the senior residents, the care-givers cannot look after each resident at all times, or carefully watch the health of the residents and provide immediate assistance for those in need, especially when the residents move around in the nursing home.

SUMMARY

In one embodiment, a person positioning and health care monitoring system comprises a monitoring center, a plurality of RFID tag devices, and a first tracking module. The monitoring center stores position data of a plurality of targets. The plurality of RFID tag devices correspond to the plurality of targets. Each RFID tag device comprises a memory and an infrared LED. The memory stores an identification (ID) number of a corresponding one of the targets. The first tracking module comprises a plurality of infrared cameras and an RFID device. The first tracking module obtains the ID numbers of the RFID tag devices by using the RFID device to communicate with the plurality of RFID tag devices. The first tracking module communicates with the monitoring center by having the RFID device send the ID numbers of the targets and orientation data corresponding to the targets to the monitoring center. After the monitoring center receives the ID numbers of the targets and the orientation data of the targets, the monitoring center determines coordinates of the targets for positioning according to coordinates of the first tracking module and the orientation data corresponding to the targets.

To better understand the above-described objectives, characteristics and advantages of the present invention, embodiments, with reference to the drawings, are provided for detailed explanations.

BRIEF DESCRIPTION OF THE DRAWINGS

The invention will be described according to the appended drawings in which.

DETAILED DESCRIPTION OF DISCLOSED EMBODIMENTS

The following description is presented to enable any person skilled in the art to make and use the disclosed embodiments, and is provided in the context of a particular application and its requirements. Various modifications to the disclosed embodiments will be readily apparent to those skilled in the art, and the general principles defined herein may be applied to other embodiments and applications without departing from the spirit and scope of the disclosed embodiments. Thus, the disclosed embodiments are not limited to the embodiments shown, but are to be accorded the widest scope consistent with the principles and features disclosed herein.

Figure 1:
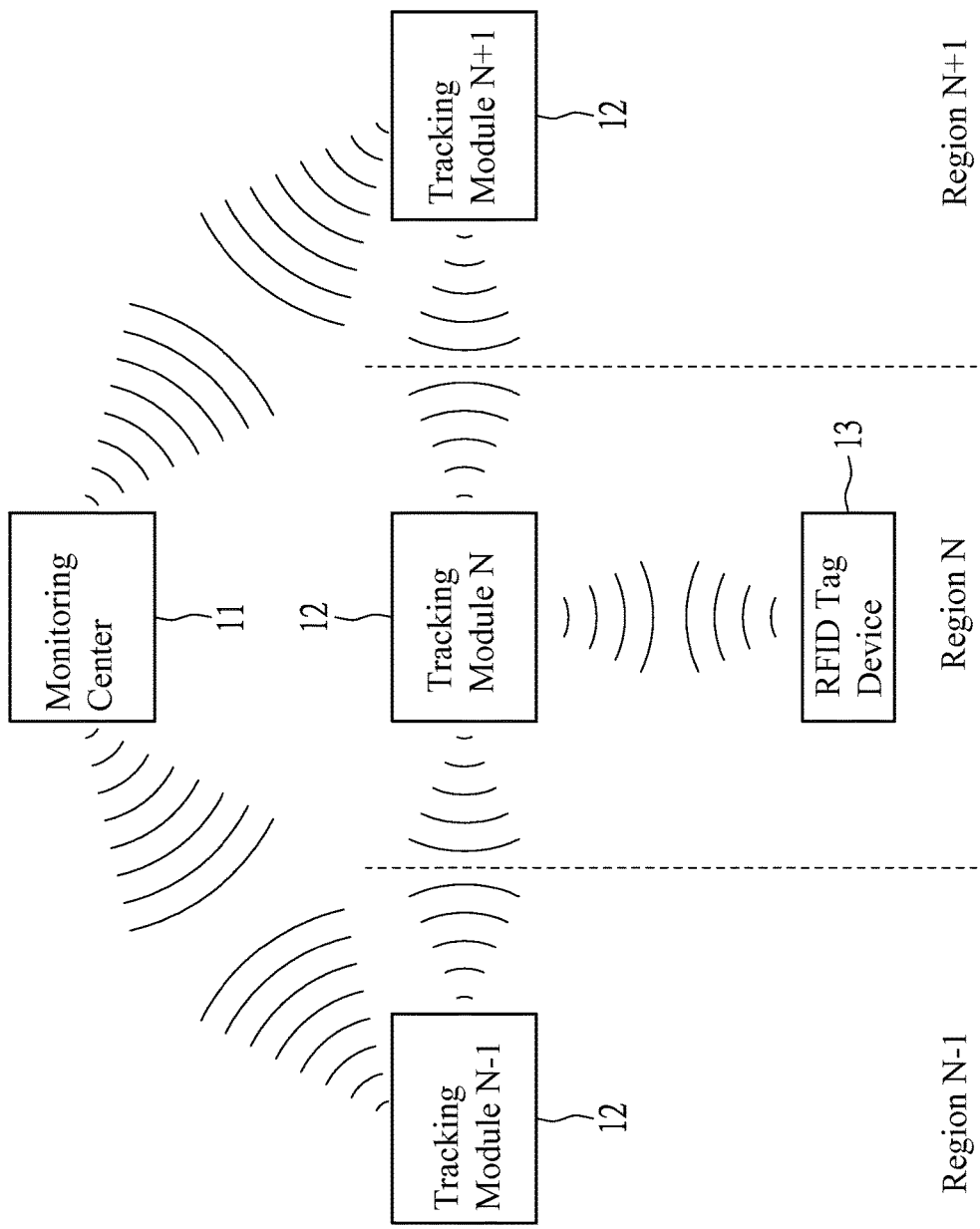
FIG. 1 is a view showing a person positioning and health care monitoring system according to one embodiment of the present invention.

Referring to FIG. 1, in at least one embodiment, a person positioning and health care monitoring system 1 comprises a monitoring center 11, at least one tracking module 12, and at least one RFID (radio-frequency identification) tag device 13. The monitoring center 11 is configured to wirelessly communicate with the at least one tracking module 12. The at least one tracking module 12 is configured to wirelessly communicate with the RFID tag device 13 and use the RFID tag device 13 to track at least one target and/or monitor the state of the at least one target. In some embodiments, the person positioning and health care monitoring system 1 comprises a plurality of tracking modules 12. The monitoring center 11 can wirelessly communicate with each tracking module 12. The tracking modules 12 can wirelessly communicate with each other. Each tracking module 12 can wirelessly communicate with the RFID tag device 13.

Referring to FIG. 1, in some embodiments, the person positioning and health care monitoring system 1 is applied to a plurality of regions (N−1, N, and N+1) and has a plurality of tracking modules 12, each of which corresponds to an region (N−1, N, or N+1).

Figure 8:
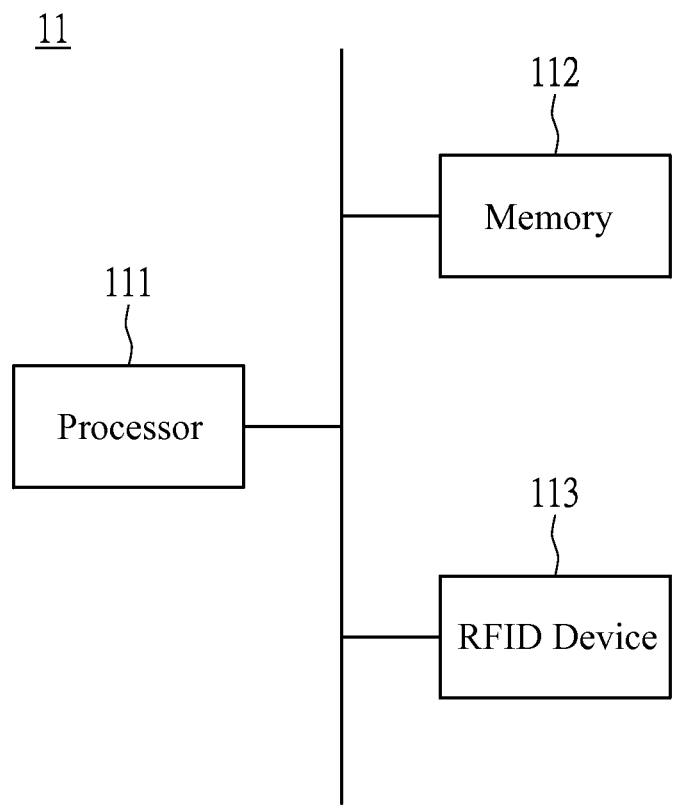
FIG. 8 is a block diagram showing a monitoring center according to one embodiment of the present invention.

Referring to FIG. 8, in some embodiments, the monitoring center 11 comprises a processor 11, a memory 112, and an RFID device 113. The processor 11 is configured to execute instructions of programs for the monitoring center 11. The memory 112 at least stores position data of at least one target. The RFID device 113 is configured to communicate with the tracking module 12. In some embodiments, the memory 112 comprises a volatile memory. In some embodiments, the memory 112 comprises non-volatile memory.

Figure 2:
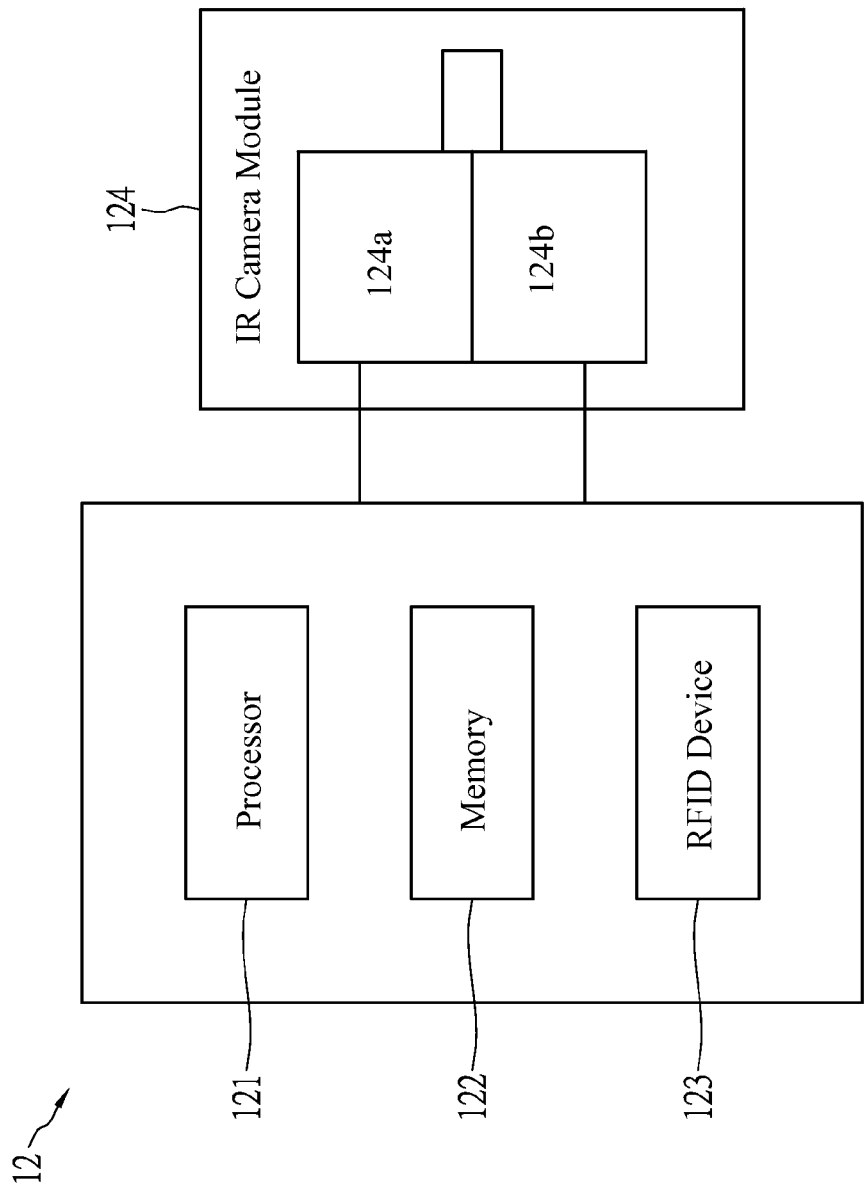
FIG. 2 is a view showing a tracking module according to one embodiment of the present invention.

Referring to FIG. 2, the tracking modules 12 comprises a processor 121, a memory 122, an RFID reader or device 123, and an infrared camera 124. The processor 121 is configured to execute instructions of programs for the tracking modules 12. The memory 122 can store programs or data. The RFID device 123 is configured to communicate with the monitoring center 11 and the RFID tag device 13. The infrared camera 124 can generate pictures, which can be used to determine orientation data (including azimuth data and elevation data) of at least one target. The orientation data can be used to drive a pitch axis tracking device 124a and a yaw axis tracking device 124b of the infrared camera 124 to track at least one target. The tracking modules 12 are configured to send azimuth data and elevation data of the pitch axis tracking device 124a and the yaw axis tracking device 124b corresponding to a tracked target to the monitoring center 11, and the monitoring center 11 can determine the coordinates of the target according to the coordinates of the infrared camera 124 and the azimuth and elevation data corresponding to the target, thereby monitoring the target.

In some embodiments, the tracking module 12 comprises a plurality of stepping motors. Each infrared camera 124 is coupled with at least one stepping motor in order to drive the corresponding infrared camera 124 to rotate up or down. In some embodiments, the tracking module 12 comprises a plurality of stepping motors, and each infrared camera 124 is coupled with at least one stepping motor in order to drive the corresponding infrared camera 124 to rotate left and right.

Figure 3:
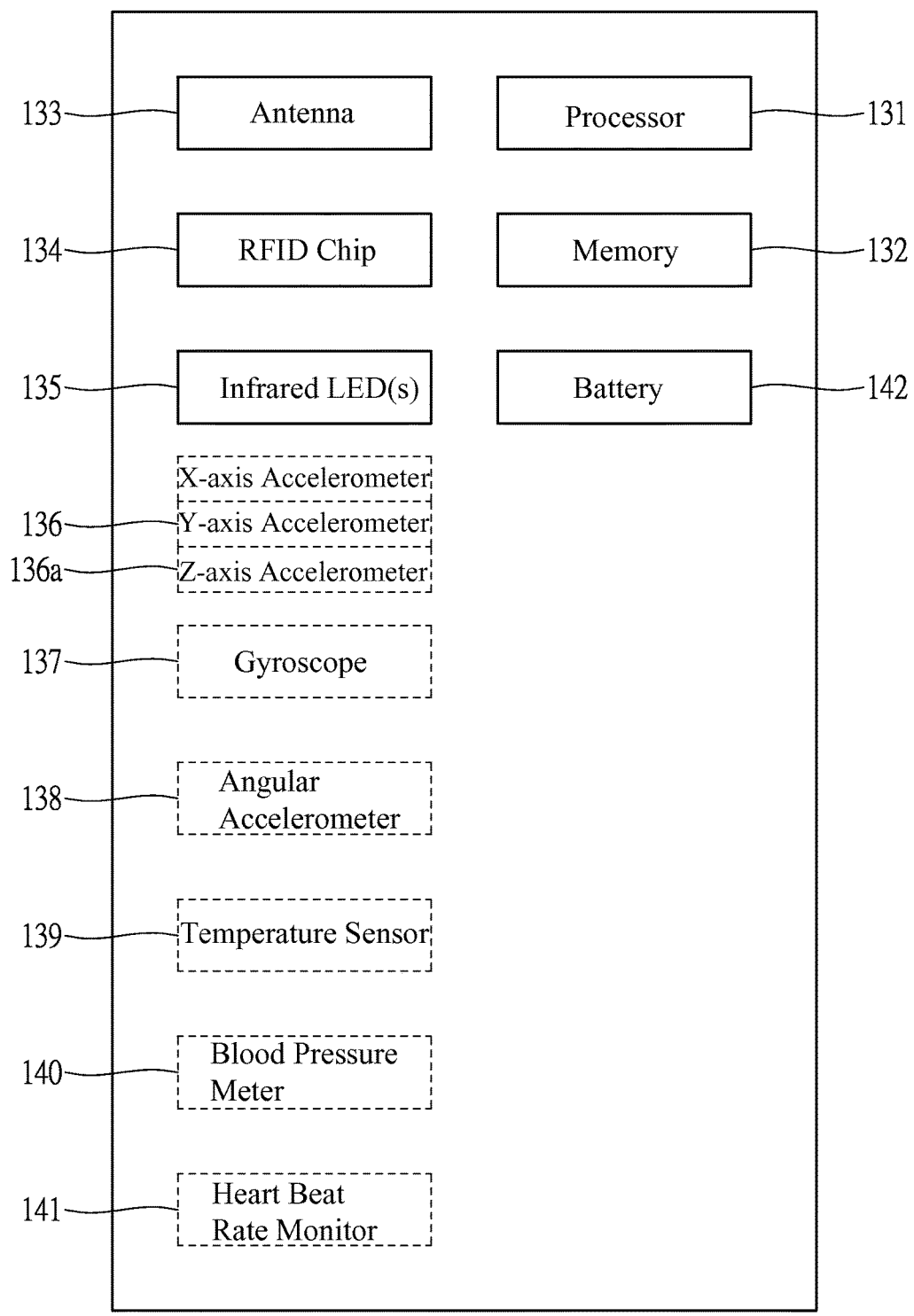
FIG. 3 is a view showing an RFID device according to one embodiment of the present invention.

Referring to FIG. 3, the RFID tag device 13 comprises a processor 131. The processor 131 of RFID tag device 13 is responsible for operating the RFID tag device 13. The RFID tag device 13 comprises a memory 132. The memory 132 can store an ID number of a target, whereby the person positioning and health care monitoring system 1 tracks a target carrying the RFID tag device 13. The RFID device 113 comprises an antenna 133 and a RFID chip 134 coupled with the antenna 133. The RFID tag device 13 uses the RFID chip 134 and the antenna 133 to communicate with the tracking module 12. In some embodiments, the tracking module 12 retrieves the target ID number stored in the memory 132 of a RFID tag device 13 through the RFID chip 134 and the antenna 133. The RFID tag device 13 comprises an infrared LED (light-emitting diode) 135. The infrared LED 135 generates light, and thereby forms a light image on a picture created by an infrared camera 124. The tracking module 12 sends the azimuth and elevation angles of an infrared camera 124 corresponding to a tracked target to the monitoring center 11, and the monitoring center 11 uses the coordinates of the infrared camera 124 and the azimuth and elevation angles corresponding to the target to determine the coordinate information of the target.

In some embodiments, the RFID tag device 13 comprises accelerometers 136. The accelerometers 136 are configured to provide instantaneous acceleration in three dimensions when a target is moving. The RFID tag device 13 transmits the three-dimensional acceleration to the tracking module 12, and the tracking module 12 transmits the three-dimensional acceleration to the monitoring center 11. If the target does not change direction, the monitoring center 11 integrates the acceleration twice to determine a relative motion vector for a time segment, thereby obtaining a path and all locations of the target. In some embodiments, the accelerometer 136 comprises a Z-axis accelerometer 136a. When the monitoring center 11 finds that acceleration provided by the Z-axis accelerometer 136a of the RFID tag device 13 on a target who was moving is less than or equal to a threshold value, the monitoring center 11 generates a warning that the target may fall over. Normally, when people stand up or walk, the Z-axis accelerometer 136a outputs a downward acceleration value of 1G or 9.8 meters per second squared, which is equivalent to the gravity acceleration on the surface of the Earth. When a target that was moving lies down or falls over on the ground, the Z-axis accelerometer 136a outputs a value of approximately zero. With such a characteristic, the monitoring center 11 can use an outputted value to determine whether a target falls over and accordingly generate a warning to relevant persons who can get to the target and provide instant help.

In some embodiments, the RFID tag device 13 comprises a gyroscope 137. The gyroscope 137 is used to measure an orientation of a target and thereby provide an instantaneous angular velocity vector. The monitoring center 11 integrates the instantaneous angular velocity information of the target from the gyroscope 137 so as to determine and obtain the data of the direction of motion at every moment. The monitoring center 11 uses the data of the direction of motion and an integrated instantaneous velocity vector from each accelerometer, and performs coordination conversion, and thereafter, relative position information of the target at every moment when the target is moving can be obtained. The monitoring center 11 finally adds up the previous relative position data and the latest relative position data to determine the path of motion. The monitoring center 11 can use the path of motion to determine when, where, and what happened during the target's journey; when and where the target moved forward, turned around, turned left, turned right, fell onto the ground, and how long the target stood up from the ground, or when the target fell again and did not stand up. Such inferred information is valuable and the monitoring center 11 can use the inferred information to seek help when the target fell over, or discover that the target had fallen over or had difficulty in walking by analyzing the inferred information and can implement a preventive measure.

In some embodiments, the RFID tag device 13 comprises at least one angular accelerometer 138. The angular accelerometer 138 can determine angular velocity according to angular acceleration. The monitoring center 11 can use the angular velocity to determine a rotation angle of the corresponding target. The angular accelerometer 138 is similar in function to the gyroscope 137 while also complementary to the gyroscope 137.

In some embodiments, the RFID tag device 13 comprises a temperature sensor 139 configured to measure a temperature of a corresponding target for the monitoring center 11 to monitor.

In some embodiments, the RFID tag device 13 comprises a blood pressure meter 140 configured to measure a blood pressure of a corresponding target for the monitoring center 11 to monitor.

In some embodiments, the RFID tag device 13 comprises a heart beat rate monitor 141 configured to measure a heart beat rate of a corresponding target for the monitoring center 11 to monitor.

In some embodiments, the RFID tag device 13 comprises a power supply 142, such as a battery, configured to supply electricity to the infrared LED 135 and the RFID tag chip.

In some embodiments, the RFID tag device 13 comprises a component, which is an infrared LED 135, an accelerometer 135, a gyroscope 137, an angular accelerometer 138, a temperature sensor 139, a blood pressure meter 140, or a heart beat rate monitor 141. A target can carry a plurality of RFID tag devices 13 with different components. In some embodiments, the RFID tag device 13 comprises a plurality of components, and the components comprise an infrared LED 135, an accelerometer 135, a gyroscope 137, an angular accelerometer 138, a temperature sensor 139, a blood pressure meter 140, and a heart beat rate monitor 141.

Figure 4:
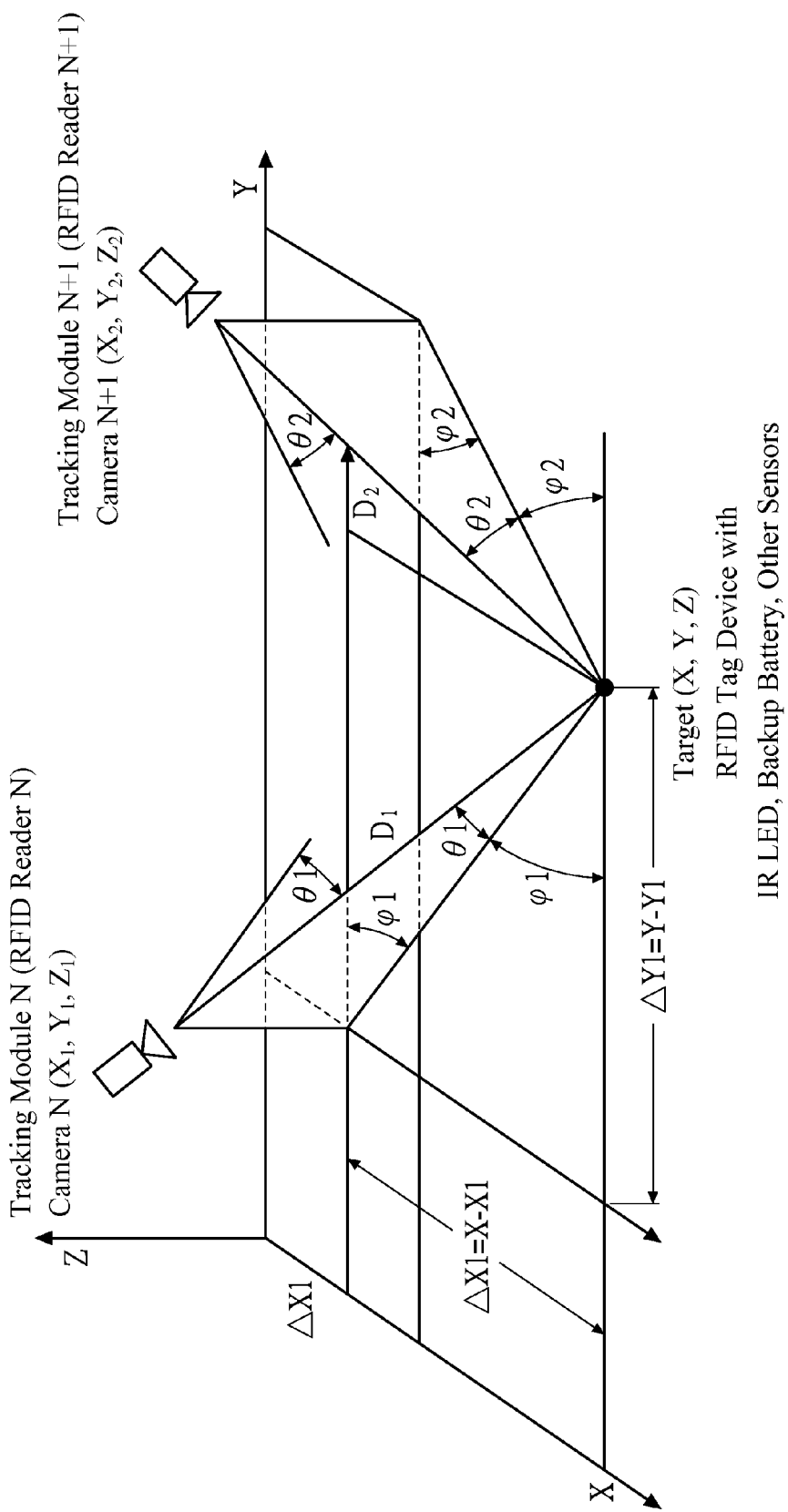
FIG. 4 is a view for demonstrating steps of calculating coordinates according to one embodiment of the present invention.

Referring to FIG. 4, the tracking module 12 is configured to obtain an orientation data corresponding to a tracked target, wherein the orientation data comprises azimuth data and elevation data. In some embodiments, the RFID tag device 13 comprises an infrared LED 135. The tracking module 12 uses the infrared camera 124 to track the infrared LED 135 of the RFID tag device 13. Information about azimuth and elevation data between the target and the infrared camera 124 is reported by the tracking module 12 and sent to the monitoring center 11 in order to determine the coordinates of the target. As shown in FIG. 4, two adjacent tracking modules 12 (N and N+1) are used as an example. If a target is between the two tracking modules 12 (N and N+1), the monitoring center 11 determines the coordinates of the target by using the pitch or elevation angles ($\theta_1$ and $\theta_2$) and yaw or azimuth angles ($\phi_1$ and $\phi_2$). Assuming that the locations of the infrared cameras 124 are represented by ($X_1$, $Y_1$) and ($X_2$, $Y_2$), the pitch or elevation angles of the infrared cameras 124 are represented by $\theta_1$ and $\theta_2$, the yaw or azimuth angles of the infrared cameras 124 are represented by $\phi_1$ and $\phi_2$, the distances of the infrared cameras 124 from the target are represented by $D_1$ and $D_2$, and the coordinates of the target are represented by (X, Y). Equations (1) can be obtained as follows:

$$\begin{cases} Y - Y_1 = D_1 \cos\theta_1 \cos\varphi_1 \\ X - X_1 = D_1 \cos\theta_1 \sin\varphi_1 \\ Y - Y_2 = D_2 \cos\theta_2 \cos\varphi_2 \\ X - X_2 = D_2 \cos\theta_2 \sin\varphi_2 \end{cases} \quad (1)$$

Equations (1) are solved and the distances ($D_1$ and $D_2$) are obtained:

$$D_1 = \frac{\begin{vmatrix} C_1 - a_{11} \\ C_2 - a_{22} \end{vmatrix}}{\begin{vmatrix} a_{11} - a_{12} \\ a_{21} - a_{22} \end{vmatrix}}, D_2 = \frac{\begin{vmatrix} a_{11} - C_1 \\ a_{21} - C_2 \end{vmatrix}}{\begin{vmatrix} a_{11} - a_{12} \\ a_{21} - a_{22} \end{vmatrix}} \quad (2)$$

The coordinates of the target (X, Y) can be obtained by substitute for $D_1$ and $D_2$ in equations (1) using equations (2).

Figure 5:
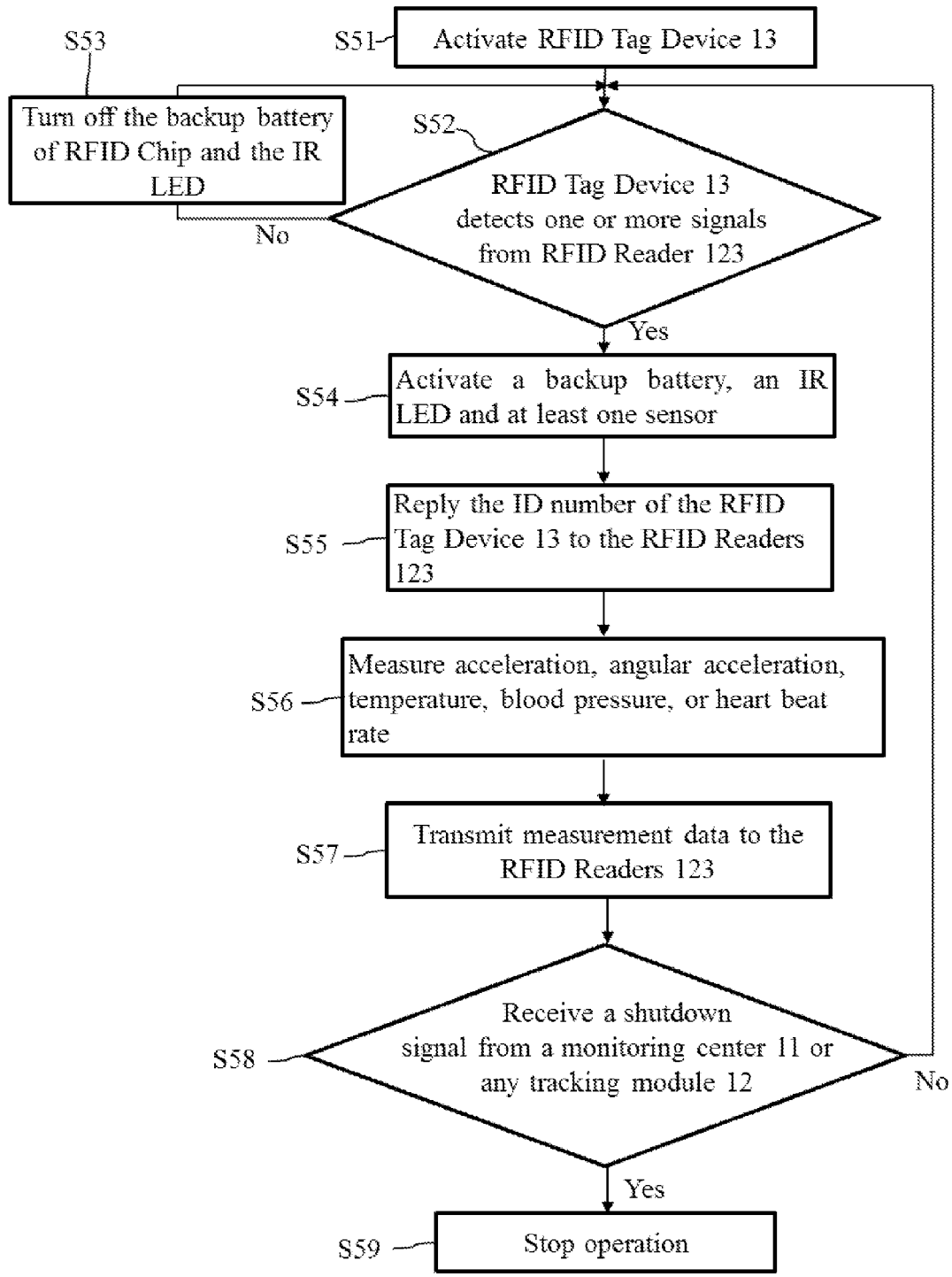
FIG. 5 is a flow chart of a RFID tag device related to a partial method of operating a person positioning and health care monitoring system according to one embodiment of the present invention.

FIG. 5 is a flow chart of a RFID tag device 13 related to a partial method of operating a person positioning and health care monitoring system 1 according to one embodiment of the present invention, wherein the partial method includes steps of activating a tracking module, turning off a tracking module, controlling the target tracking, and transmitting information. In Step S51, the RFID tag device 13 is activated. In Step S52, the RFID tag device 13 checks whether a signal or message from the RFID reader 123 of any one of the tracking modules 12 is received. In Step S53, if the RFID tag device 13 determines that no message from the RFID reader 123 of any one of tracking modules 12 is received, then the RFID tag device 13 cuts off a supply to RFID chip and infrared LED from a backup battery in order to preserve energy. In Step S54, if the RFID tag device 13 has received a signal or message from the RFID reader 123 of any one of the tracking modules 12, the RFID tag device 13 starts using battery power to activate at least one sensors and an infrared LED for tracking by utilizing the infrared camera 124 of the RFID device 123 of tracking module 12. In Step S55, the RFID tag device 13 transmits the ID number of the target to the tracking modules 12. In Step S56, the RFID tag device 13 uses at least one of the above-mentioned sensors or components, such as accelerometers 135, a gyroscope 137, angular accelerometers 138, a temperature sensor 139, a blood pressure meter 140, and a heart beat rate monitor 141, to obtain measurement data by measuring acceleration, angular velocity, angular acceleration, temperature, blood pressure, or a heart beat rate. In Step S57, the RFID tag device 13 transmits the measurement data to the RFID readers 123 of tracking modules 12. In Step S58, the RFID tag device 13 checks whether there is a shutdown signal or message from the monitoring center 11 or any tracking module 12. If no shutdown signal or message is received, the method proceeds to Step S52. In Step S59, if the RFID tag device 13 receives a shutdown signal or message, the RFID tag device 13 stops functioning.

Figure 6:
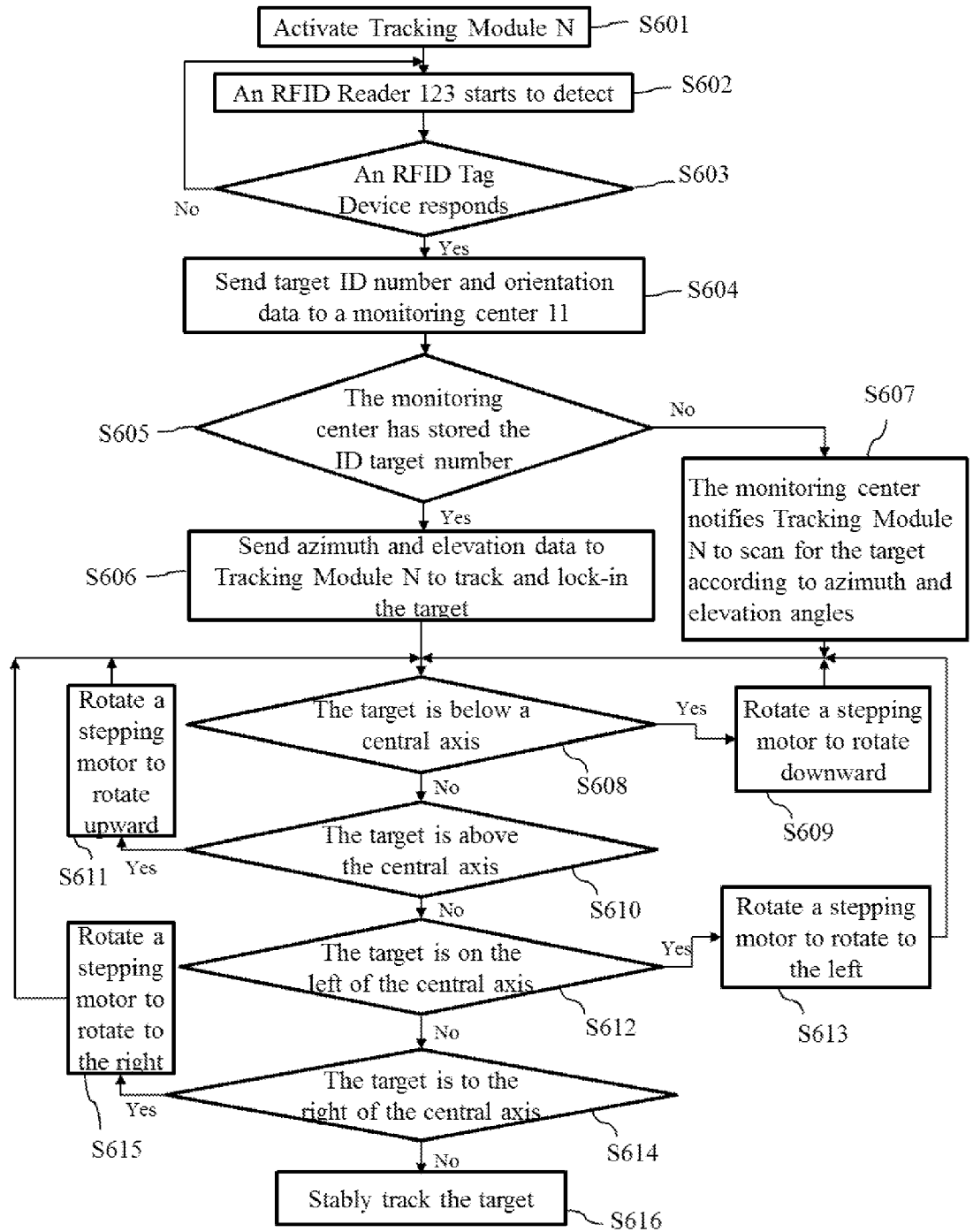
FIG. 6 is a flow chart of a tracking module N related to a partial method of operating a person positioning and health care monitoring system according to one embodiment of the present invention.

FIG. 6 is a flow chart of a tracking module N related to a partial method of operating a person positioning and health care monitoring system 1 according to one embodiment of the present invention, wherein the partial method is related to the operations of a pitch axis tracking device 124a, a yaw axis tracking device 124b, and stepping motors.

In Step S601, the tracking module N is activated.

In Step S602, the RFID device 123 of the tracking module N carries out detections.

In Step S603, the RFID device 123 of the tracking module N checks whether there is a response from any one of the RFID tag devices 13 or responses from a plurality of RFID tag devices 13. If no response has been received, the RFID device 123 of the tracking module N continues performing detections.

In Step S604, the RFID device 123 of the tracking module N may receive a response from any one of the RFID tag devices 13 or responses from RFID tag devices 13, and receives the ID numbers of the targets sent by new RFID tag devices 13. Next, the tracking module N transmits the received target ID numbers to the monitoring center 11.

In Step S605, the monitoring center 11 uses the target ID numbers to determine if the coordinates of any of the corresponding targets are recorded within recent time; for example, 3 seconds (which is not a limitation to the present invention) from receiving the target ID numbers.

In Step S606, if the monitoring center 11 has the coordinates of the targets recorded within recent time, for example, 3 seconds (which is not a limitation to the present invention) from receiving the target ID numbers, then the monitoring center 11 sends azimuth and elevation angles of the targets relative to the tracking module N to the tracking module N, so that the tracking module N can determine an average elevation angle (E) and an average azimuth angle (A) as the gimbal angle commands to the infrared cameras 124a and 124b to track and lock-in the targets.

In Step S607, if the monitoring center 11 does not have the coordinates of the targets recorded within recent time, for example, 3 seconds (which is not a limitation to the present invention) from receiving the target ID numbers, the monitoring center 11 instructs the tracking module N to use the present azimuth and elevation angles of the infrared camera as origins and begins rotating the infrared camera in a spiral manner outwards from the origins so as to gradually increase the search region for the targets.

The tracking module N uses the position of a light image of a picture from an infrared camera 124 in order to determine an average elevation angle (E) and an average azimuth angle (A) for the corresponding targets. If both the absolute values of E and A are less than the corresponding gimbal search limits, then the method proceeds to Step S608; otherwise, the method proceeds to Step S701 of FIG. 7.

In Step S608, if E is less than −0.5 degree (which is not a limitation to the present invention), it indicates that the target is below the elevation axis of the infrared camera 124a of the tracking module N. In Step S609, a corresponding stepping motor is rotated to turn the gimbal angle of the infrared camera 124a to the elevation angle E so as to point the elevation axis of the infrared camera 124a to the elevation center of targets.

In Step S610, if E is greater than 0.5 degree (which is not a limitation to the present invention), the value indicates that the target is above the elevation axis of the infrared camera 124a of the tracking module N. In Step S611, a corresponding stepping motor is rotated to turn the gimbal angle of infrared camera 124a to the elevation angle E so as to point the elevation axis of the infrared camera 124a to the elevation center of targets.

In Step S612, if the average azimuth value (A) of the target(s) is less than −0.5 degree (which is not a limitation to the present invention), the value indicates that the target is on the left side of the azimuth axis of the infrared camera 124b of the tracking module N. In Step S613, a corresponding stepping motor is rotated to turn the gimbal angle of infrared camera 124b to the azimuth angle A so as to point the azimuth axis of the infrared camera 124b to the azimuth center of targets.

In Step S614, if the average azimuth value (A) of the target(s) is greater than 0.5 degree (which is not a limitation to the present invention), the value indicates that the target is on the right side of the central axis of the infrared camera 124b of the tracking module N. In Step S615, a corresponding stepping motor is rotated to turn the infrared camera 124b to the gimbal angle A so as to point until the azimuth axis of the infrared camera 124b to the azimuth center of targets.

In Step S616, the above Steps S608 to S614 are applied to adjust the gimbal angles of infrared camera 124 until both the tracking errors to the centers of targets in both the elevation and azimuth axes of the infrared camera 124 are less than 0.5 degree (which is not a limitation to the present invention) so that the target(s) can be properly tracked.

Figure 7:
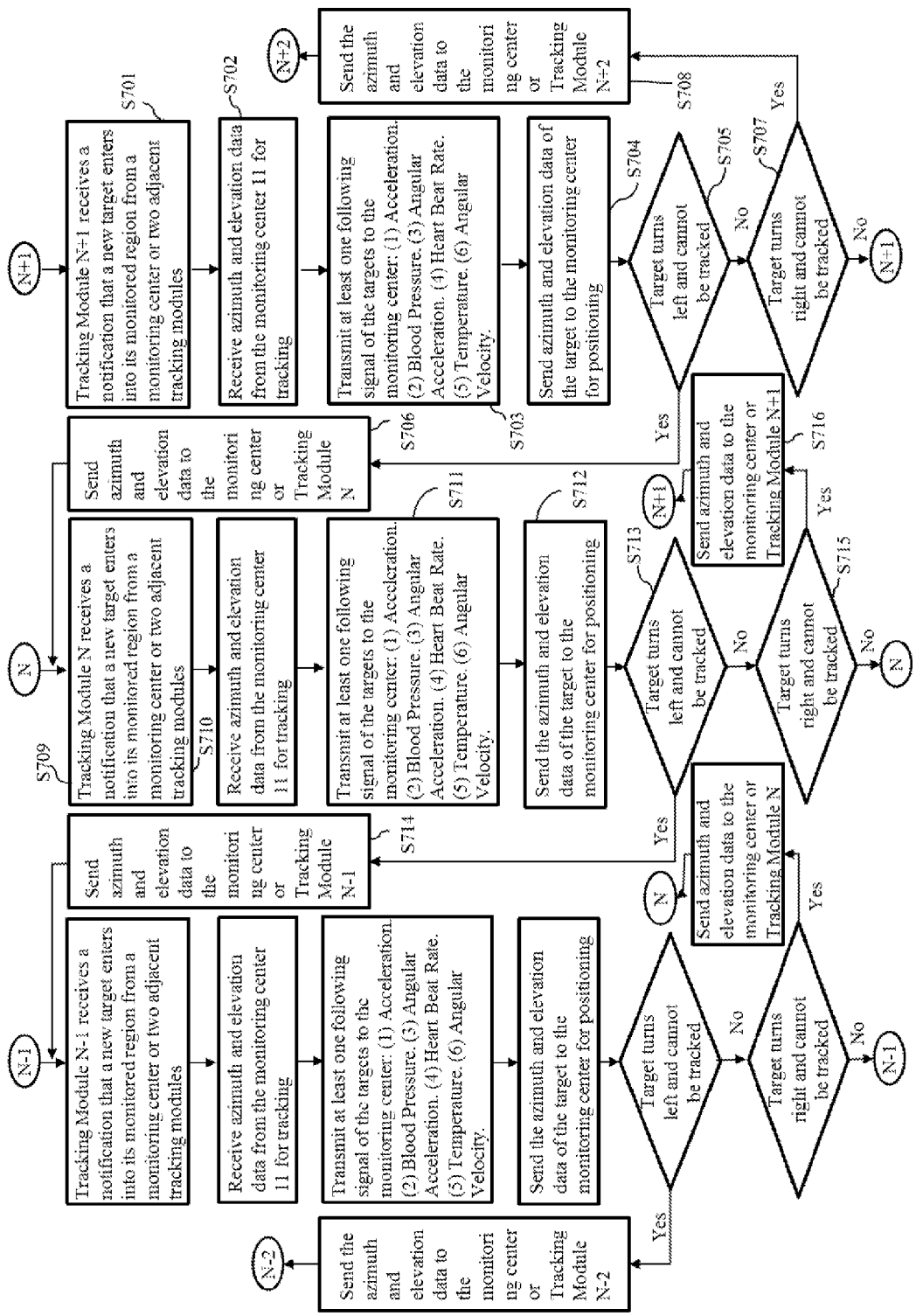
FIG. 7 is a flow chart among the tracking modules related to a partial method of operating a person positioning and health care monitoring system according to one embodiment of the present invention.

FIG. 7 is a flow chart among the tracking modules related to a partial method of operating a person positioning and health care monitoring system 1 according to one embodiment of the present invention, wherein the partial method is related to the tracking control and the information exchange between two tracking modules. Referring to FIG. 7, the person positioning and health care monitoring system 1 comprises a plurality of tracking modules, which includes a tracking module N−1, a tracking module N, and a tracking module N+1. The plurality of tracking modules respectively monitor different regions, wherein at least some of which can overlap.

In Step S701, the tracking module N+1 is notified by the monitoring center 11 or two adjacent tracking modules that a new target is entering into the monitored region. In Step S702, the tracking module N+1 determines the average values of azimuth and elevation angles (i.e. A and E in previous) of all targets under its monitor (including targets that have already been monitored and a new target that has not yet been monitored) according to orientation data, for example within a three second timeframe (which is not a limitation to the present invention), of all targets, and respectively drives the tracking devices 124a and 124b coupled with the infrared camera 124 of the tracking module N+1 according to the average values of azimuth and elevation angles so as to track the targets.

In Step S703, the tracking module N+1 retrieves data of acceleration, angular acceleration, temperature, blood pressure, or heart beat rate of the targets. Next, the tracking module N+1 transmits data of at least one of the acceleration, angular acceleration, temperature, blood pressure, or heart beat rate to the monitoring center 11.

In Step S704, the tracking module N+1 uploads the latest orientation data of the new target to the monitoring center 11 in order to determine the coordinates of the target. In some embodiments, the tracking module N+1 continuously uploads the latest orientation data of the targets to the monitoring center 11 so as to allow the monitoring center 11 to determine their coordinates.

In Step S705, the tracking module N+1 determines whether one or more targets move out of left limit and leave the region monitored by it (i.e. determines whether the azimuth gimbal angle of the IR camera tracking module 124b rotate to the left is larger than 60 degrees relative to the central axis of the infrared camera when it is at the initialization position; however, the present invention is not limited to the afore-mentioned number of degrees).

In Step S706, the tracking module N+1 determines that one or more targets move out of left limit and leave the region monitored by it (i.e. determines that the azimuth gimbal angle of the IR camera tracking module 124b rotate to the left is larger than 60 degrees relative to the central axis of the infrared camera when it is at the initialization position; however, the present invention is not limited to the afore-mentioned number of degrees) and enter into the region monitored by the tracking module N. The tracking module N+1 notifies the monitoring center 11 that the target(s) is not in its monitored region and transmits the latest orientation data, including azimuth and elevation data, to the monitoring center 11 or the tracking module N.

In Step S707, the tracking module N+1 determines whether one or more targets move out of right limit and leave its monitored region (i.e. determines whether the azimuth angle of the IR camera tracking module 124b rotate to the right is larger than 60 degrees relative to the central axis of the infrared camera when it is at the initialization position; however, the present invention is not limited to the afore-mentioned number of degrees).

In Step S708, the tracking module N+1 determines that one or more targets move out of right limit and leave the region monitored by it (i.e. determines that the azimuth angle of the IR camera tracking module 124b rotate to the right is larger than 60 degrees relative to the central axis of the infrared camera when it is at the initialization position; however, the present invention is not limited to the afore-mentioned number of degrees) and enter into the region monitored by the tracking module N+2. The tracking module N+1 notifies the monitoring center 11 that the target(s) is not in its monitored region and transmits the latest orientation data, including azimuth and elevation data, to the monitoring center 11 or the tracking module N+2.

In Step S709, the tracking module N receives notification that a new target is entering its monitored region from the monitoring center 11 or one of the two adjacent tracking modules.

In Step S710, the tracking module N receives the latest orientation data, including azimuth and elevation data, of the corresponding RFID tag device 13 from the monitoring center 11 in order to track the target. The Step S710 is similar to the Step S702 of FIG. 6.

In Step S711, the tracking module N retrieves data of acceleration, angular acceleration, temperature, blood pressure, or heart beat rate of the targets. Next, the tracking module N transmits data of at least one of the acceleration, angular acceleration, temperature, blood pressure, or heart beat rate to the monitoring center 11.

In Step S712, the tracking module N uploads the latest orientation data of the new target to the monitoring center 11 in order to determine the coordinates of the target. In some embodiments, the tracking module N continuously uploads the latest orientation data of the targets to the monitoring center 11 so as to allow the monitoring center 11 to determine their coordinates.

In Step S713, the tracking module N determines whether one or more targets move out of left limit, leave the region monitored by it, and enter into the monitored region of the tracking module N−1 (i.e. determines whether the azimuth gimbal angle of the IR camera tracking module 124b rotate to the left is larger than 60 degrees relative to the central axis of the infrared camera when it is at the initialization position; however, the present invention is not limited to the afore-mentioned number of degrees).

In Step S714, the tracking module N determines that one or more targets leave the region monitored by it (i.e. determines that the azimuth gimbal angle of the IR camera tracking module 124b rotate to the left is larger than 60 degrees relative to the central axis of the infrared camera when it is at the initialization position; however, the present invention is not limited to the afore-mentioned number of degrees). The tracking module N notifies the monitoring center 11 and transmits the latest orientation data, including azimuth and elevation data, to the tracking module N−1. In some embodiments, the tracking module N transmits the latest orientation data, including azimuth and elevation data, of the targets to the monitoring center 11.

In Step S715, the tracking module N determines whether one or more targets move out of right limit, leave its monitored region, and enter into the monitored region of the tracking module N+1 (i.e. determines whether the azimuth gimbal angle of the IR camera tracking module 124b rotate to the right is larger than 60 degrees relative to the central axis of the infrared camera when it is at the initialization position; however, the present invention is not limited to the afore-mentioned number of degrees).

In Step S716, the tracking module N determines that one or more targets leave its monitored region (i.e. determines that the azimuth gimbal angle of the IR camera tracking module 124b rotate to the right is larger than 60 degrees relative to the central axis of the infrared camera when it is at the initialization position; however, the present invention is not limited to the afore-mentioned number of degrees) and enter into the region monitored by the tracking module N+1. The tracking module N notifies the monitoring center 11 and transmits the latest orientation data, including azimuth and elevation data, of the targets to the tracking module N+1. In some embodiments, the tracking module N transmits the latest orientation data, including azimuth and elevation data, of the targets to the monitoring center 11.

The tracking operations and steps performed when a target moves between regions monitored by the tracking module N−2, the tracking module N−1 and the tracking module N are similar to the above-mentioned steps, so redundant descriptions are omitted for sake of brevity.

In at least one embodiment, the person positioning and health care monitoring system can be used indoors and outdoors, and quickly and effectively tracks and locates the position of people. In some embodiments, the person positioning and health care monitoring system can be configured as an elderly care system. In some embodiments, the tracking module may have an infrared camera and a person can carry a plurality of RFID devices, which may be disposed on his/her chest, back, wrist or pants, and each RFID device includes an infrared LED, an accelerometer, a gyroscope, an angular accelerometer, a temperature sensor, a blood pressure meter, and a heart beat rate monitor. The person positioning and health care monitoring system can track people for day and night. The people are tracked by ID number, not by image analysis. Moreover, the system can measure health conditions of tracked people so that the system can reduce manpower. Therefore, the person positioning and health care monitoring system can integrate the functions of an RFID device, extend monitoring regions, quickly identify targets, does not require image analysis technologies, and greatly improves efficiency.

It will be apparent to those skilled in the art that various modifications and variations can be made to the disclosed embodiments. It is intended that the specification and examples be considered as exemplary only, with a true scope of the disclosure being indicated by the following claims and their equivalent.

What is claimed is:

1. A person positioning and health care monitoring system comprising:
   a monitoring center storing position data of a plurality of targets;
   a plurality of RFID tag devices corresponding to the plurality of targets, each RFID tag device comprising a memory and an infrared LED, the memory storing an identification (ID) number of a corresponding one of the targets; and
   a first tracking module comprising a plurality of infrared cameras and an RFID device;
   wherein the first tracking module obtains, from the memory of each of the RFID tag devices, the identification (ID) numbers of the RFID tag devices by using the RFID device to communicate with the plurality of RFID tag devices;
   wherein the first tracking module communicates with the monitoring center by the RFID device so as to send the identification (ID) numbers of the targets and orientation data corresponding to the targets to the monitoring center;
   wherein after the monitoring center receives the identification (ID) numbers of the targets and the orientation data of the targets, the monitoring center determines coordinates of the targets for positioning according to both coordinates of the first tracking module and the orientation data corresponding to the targets; and
   wherein the plurality of infrared cameras generates a plurality of pictures of the targets to determine the orientation data,
   wherein the orientation data comprises azimuth and elevation angles of the targets.

2. The person positioning and health care monitoring system of claim 1, wherein the first tracking module comprises a plurality of stepping motors for each infrared camera, wherein each of the plurality of stepping motors is configured to rotate the corresponding infrared camera up, down, left, and right so as to track the targets.

3. The person positioning and health care monitoring system of claim 2, wherein each infrared camera is rotated according to the tracking error angles of an infrared image of a targets-picture of the infrared camera from the average values of target azimuth data and elevation data in the azimuth and elevation axes of the infrared camera.

4. The person positioning and health care monitoring system of claim 1, wherein when the first tracking module obtains and determines the average values of the new orientation data of the targets, the first tracking module sends the new orientation data of the targets to the monitoring center, wherein the new orientation data comprises azimuth and elevation angles.

5. The person positioning and health care monitoring system of claim 1, further comprising a second tracking module, wherein the first tracking module and the second tracking module are configured to respectively monitor different first and second regions, wherein when one of the targets moves from the first region monitored by the first tracking module to the second region, the first tracking module send the latest orientation data of the one of the targets to the monitoring center or the second tracking module, wherein the latest orientation data comprises azimuth and elevation angles.

6. The person positioning and health care monitoring system of claim 5, wherein the monitoring center sends the latest orientation data to the second tracking module.

7. The person positioning and health care monitoring system of claim 5, wherein when the second tracking module detects the one of the targets, the second tracking module reads the identification (ID) number of the one of the targets.

8. The person positioning and health care monitoring system of claim 7, wherein after the second tracking module sends the identification (ID) number and new orientation data of the one of the targets to the monitoring center and the monitoring center receives the identification (ID) number and the new orientation data, the monitoring center determines coordinates of the one of the targets according to coordinates of the second tracking module and the new orientation data provided by the corresponding RFID device for positioning.

9. The person positioning and health care monitoring system of claim 1, wherein each RFID tag device comprises a temperature sensor and each RFID tag device uses the corresponding RFID device to send a measured temperature to the monitoring center.

10. The person positioning and health care monitoring system of claim 1, wherein each RFID tag device comprises a blood pressure meter and each RFID tag device uses the corresponding RFID device to send a measured blood pressure to the monitoring center.

11. The person positioning and health care monitoring system of claim 1, wherein each RFID tag device comprises a heart beat rate monitor and each RFID tag device uses the corresponding RFID device to send a measured heart beat rate to the monitoring center.

12. The person positioning and health care monitoring system of claim 1, wherein each RFID tag device comprises a Z-axis accelerometer and each RFID tag device uses the corresponding RFID device to send a measured Z-axis acceleration to the monitoring center.

13. The person positioning and health care monitoring system of claim 12, wherein if one of the Z-axis accelerations is less than or equal to a threshold, the monitoring center generates a warning.

14. The person positioning and health care monitoring system of claim 1, wherein the monitoring center is configured to send a shutdown signal to one of the RFID tag devices so as to turn off the one of the RFID tag devices.

15. The person positioning and health care monitoring system of claim 1, wherein each RFID tag device comprises a power supply configured to supply electricity to the infrared LED and the RFID tag chip.

* * * * *